United States Patent
Kobayashi et al.

(10) Patent No.: US 6,476,250 B1
(45) Date of Patent: Nov. 5, 2002

(54) OPTICALLY ACTIVE FLUORINATED BINAPHTHOL DERIVATIVE

(75) Inventors: Shu Kobayashi, Tokyo (JP); Haruro Ishitani, Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/889,407

(22) PCT Filed: Nov. 17, 2000

(86) PCT No.: PCT/JP00/08126

§ 371 (c)(1),
(2), (4) Date: Sep. 13, 2001

(87) PCT Pub. No.: WO01/36359

PCT Pub. Date: May 25, 2001

(30) Foreign Application Priority Data

Nov. 17, 1999 (JP) ............................................. 11-327423

(51) Int. Cl.[7] ............................................. C07C 229/00
(52) U.S. Cl. ............................... 560/35; 556/1; 556/54; 556/56; 556/80; 556/108; 556/174; 556/406; 568/1; 568/719
(58) Field of Search ........................ 568/719, 1; 556/1, 556/54, 108, 175, 406, 80, 56; 560/35

(56) References Cited

FOREIGN PATENT DOCUMENTS

EP    359 046    10/1990

OTHER PUBLICATIONS

Kobayashi, Organic Letters, vol. 2(9), pp. 1225–1227 (May 4, 2000).*
Tian, Tetrahedron Letters, vol. 41, pp. 8813–8816 (Nov. 4, 2000).*
Chen, Tetrahedron Letters, vol. 42, pp. 4275–4278 (2001).*
Ishitani et al., J. Am. Chem. Soc., vol. 122, No. 34, pp. 8180–8186 (2000).

* cited by examiner

*Primary Examiner*—Michael L. Shippen
(74) *Attorney, Agent, or Firm*—Wenderoth, Lind & Ponack, L.L.P.

(57) ABSTRACT

In order to provide a novel optically active binaphthol derivative useful as an asymmetric catalyst or the like, with which a higher reaction yield and a higher optical yield (selectivity) may be attained in asymmetric synthesis, an asymmetric catalyst using the same and a method of asymmetric synthesis, an optically active fluorinated binaphthol derivative represented by the following formula (I)

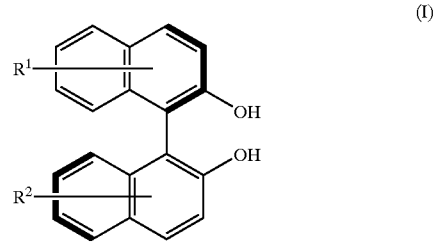

(I)

(wherein $R^1$ and $R^2$ each represent a fluorinated hydrocarbon group) was synthesized.

5 Claims, No Drawings

OPTICALLY ACTIVE FLUORINATED BINAPHTHOL DERIVATIVE

TECHNICAL FIELD

The invention of the present application relates to an optically active fluorinated binaphthol derivative. More specifically, it relates to an optically active fluorinated binaphthol derivative, which is useful as an asymmetric catalyst or the like with excellent reaction yield and optical selectivity, an asymmetric metal catalyst using the same, and further, a method of asymmetric synthesis using this asymmetric metal catalyst.

BACKGROUND ART

Asymmetric synthesis has attracted much interest as a method of synthesizing organic compounds that are used in medical drugs or the like as biologically active substances. Optically active binaphthols have been known as substances constituting catalysts or reaction accelerators for such asymmetric synthesis.

For example, asymmetric metal complexes formed by the reaction of optically active binaphthols and metal compounds have been known.

However, for the optically active binaphthols proposed so far, such as halogen-substituted binaphthols, improvements of reaction yield and optical yield (selectivity) are not easy when used in asymmetric synthesis reaction, causing problems for practical use.

Accordingly, the invention of the present application aims to provide, upon solving the aforesaid problems of the prior technique, a novel optically active binaphthol derivative useful as an asymmetric catalyst or the like, with which higher reaction yield and higher optical yield (selectivity) may be attained in asymmetric synthesis reaction, an asymmetric catalyst using the same and a method of asymmetric synthesis.

DISCLOSURE OF INVENTION

As a solution of the above-mentioned problems, the invention of the present application first provides an optically active fluorinated binaphthol derivative represented by the following formula (I)

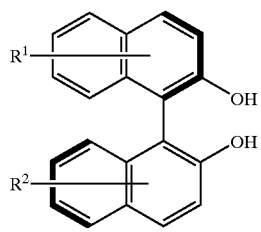

(I)

(wherein $R^1$ and $R^2$ each represent a fluorinated hydrocarbon group), and secondly provides the optically active fluorinated binaphthol derivative, wherein the fluorinated hydrocarbon group of $R^1$ and $R^2$ is a perfluoroalkyl group.

Further, the invention of the present application thirdly provides a method for producing the optically active fluorinated binaphthol derivative of the first or second invention, comprising the substitution of halogen atom (X) of an optically active halogenated binaphthol derivative represented by the following formula (II)

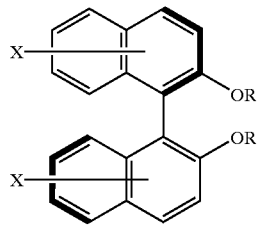

(II)

(wherein x represents a halogen atom, and R represents a protective group) with a fluorinated hydrocarbon group, and the elimination of the protective group (R).

The invention of the present application fourthly provides an asymmetric metal catalyst comprising the optically active fluorinated binaphthol derivative of the first or second invention and a metal, and fifthly, an asymmetric metal catalyst, wherein the metal is at least one element selected from the group consisting of boron, aluminum, titanium, zirconium, lanthanoid elements, gallium, bismuth, silicon and tin, is provided.

Further, the invention of the present application sixthly provides a method of asymmetric organic synthesis, comprising the formation of carbon-carbon bond using the asymmetric metal catalyst of the fourth or fifth invention.

BEST MODE FOR CARRYING OUT THE INVENTION

The invention of the present application has the above-mentioned characteristics; hereinafter the embodiments thereof are described.

First, in the invention of the present application, the optically active fluorinated binaphthol derivative represented by the above-mentioned formula (I) is provided. In this derivative, symbols $R^1$ and $R^2$ in formula (I) are fluorinated hydrocarbon groups that refer to hydrocarbon groups with hydrogen atoms substituted with fluorine atoms. As the hydrocarbon groups, saturated or unsaturated aliphatic hydrocarbon groups are considered. The fluorinated hydrocarbon groups in the above-mentioned formula (I) of the invention are indicated to be these groups substituted with fluorine atoms. Specifically, perfluoroalkyl groups are preferable as the fluorinated hydrocarbon groups. Examples thereof include —$CF_3$, —$C_2F_5$, —$C_2F_3$, —$C_3F_7$ and the like.

Such fluorinated hydrocarbon groups may be bound to various positions of a naphthalene ring of the binaphthol; typical examples would be those bound to the symmetric positions such as 6,6'- and 3,3'-.

Of course, in the optically active fluorinated binaphthol derivative of the invention, although not shown in the formula, substituents may also be bound to the naphthalene ring.

Further, the above-mentioned fluorinated hydrogen group is not limited to one on each naphthalene ring, but may be multiple groups bound to various positions of the naphthalene ring, as required.

The foregoing optically active fluorinated binaphthol derivative of the invention may be produced by the substitution of the halogenated binaphthol derivative represented by formula (II), as described previously.

To describe such method more specifically, for example, in the present invention, (R)-6,6'-(α,α,α)-trifluoromethyl-2, 2'-dihydroxy-1,1'-binaphthyl (compound 1) represented by the following formula

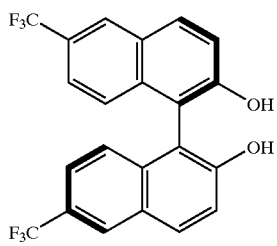

1 is provided, which may be produced by the substitution of the halogen atom with a fluorinated hydrocarbon group as shown, for example, in the following reaction scheme.

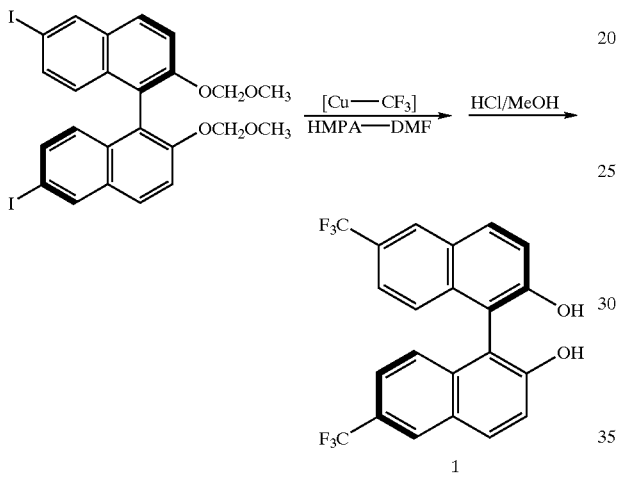

1

By the same process, for example, (R)-3,3'-(α,α,α)-trifluoromethyl-2,2'-dihydroxy-1,1'-binaphthyl (compound 5) represented by the following formula

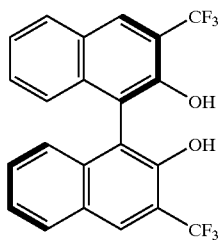

5 may also be produced.

The optically active halogenated binaphthol derivative of the above-mentioned formula (II) may easily be prepared as a commercial product or by known processes. Further, needless to say, when the protective group (R) is unnecessary, a compound having —OH as such may be used as a starting material. The substitution reaction is not limited to the foregoing process, and various processes are available.

For example, in the process represented by the above-mentioned reaction scheme, a methoxymethyl group is used as the protective group (R). However, various groups may be used as this protective group. Further, the diiodo substitution product used as the starting material may be synthesized from the corresponding dibromobinaphthol. Detailed examples of the reaction are described in the Examples section.

For example, the optically active fluorinated binaphthol derivative of the present invention obtained by the foregoing method may be used effectively as the asymmetric auxiliary group or the asymmetric ligand in asymmetric synthesis. That is, asymmetric catalysts comprising the optically active fluorinated binaphthol derivative and metal are provided by the invention. In this case, the metal may be, for example, boron, aluminum, titanium zirconium, lanthanoid elements (scandium, ytterbium, lanthanum and the like), gallium, bismuth, silicon, tin and the like. These metallic elements may constitute the asymmetric metal catalyst by being mixed or reacted with the optically active fluorinated binaphthol derivative in a solvent in the form of halides, alkoxides, or complexes.

Such asymmetric catalyst may further contain an appropriate coordination compound or active compound. Examples thereof include amines, imidazoles, phosphines and the like.

Such asymmetric metal catalysts may be used effectively in asymmetric synthesis reaction by forming carbon-carbon bond through, for example, reactions such as aldol condensation, Diels-Alder reaction, alkylation, allylation or the like. The yield of asymmetric synthesis as well as the optical yield and the selectivity become extremely high.

Accordingly, Examples are demonstrated below to describe the embodiments of the present invention in more detail.

EXAMPLES

Example 1

(R)-6,6'-(α,α,α)-trifluoromethyl-2,2'-dihydroxy-1,1'-binaphthyl as the above described compound 1 was synthesized according to the following reaction scheme.

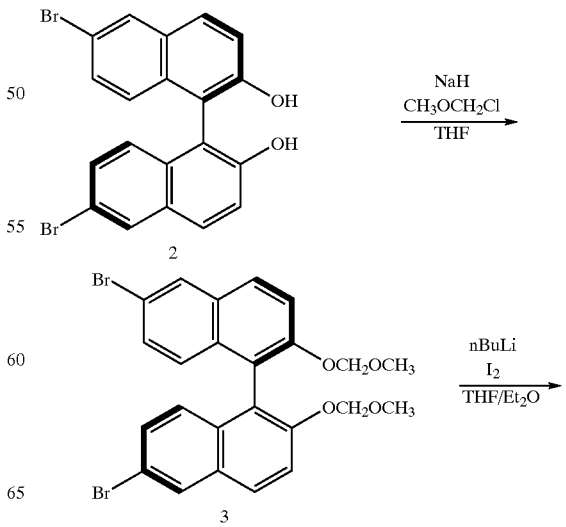

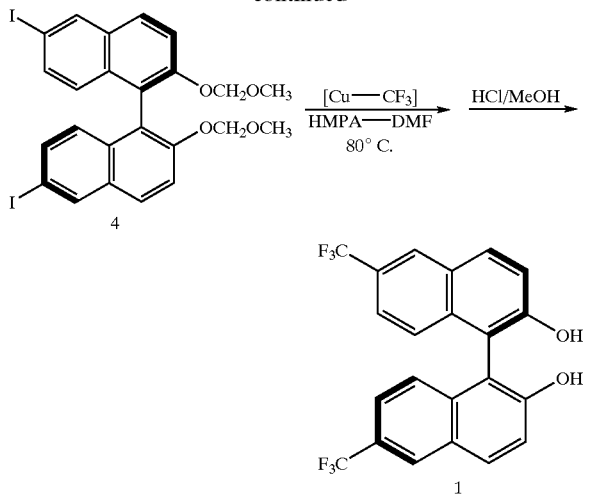

(A) Synthesis of Compound 3: (R)-6,6'-Dibromo-2,2'-di(methoxymethyl)oxy-1,1'-binaphthyl An oil suspension of sodium hydride (60%; 9.0 g, 225 mmol) was washed with petroleum ether, and dried, after which anhydrous tetrahydrofuran (150 ml) was added. After the solution was cooled to 0° C., an anhydrous tetrahydrofuran solution (soluble amount) of (R)-6,6'-dibromo-2,2'-dihydroxy-1,1'-binaphthyl (compound 2; 10 g, 22.5 mmol) was added dropwise. After the completion of the dropwise addition, the mixture was stirred at the same temperature for 1 hour, after which chloromethylmethyl ether (17.1 ml, 225 mmol) was added. This mixture was stirred at room temperature until the starting material, compound 2, could no longer be detected by TLC.

After a small amount of methanol was added to terminate the reaction, ethyl acetate and a saturated aqueous solution of ammonium chloride were added for distribution. Subsequently, the organic layer was washed with water and a saturated aqueous solution of sodium chloride, successively. The organic layer was thoroughly dried over anhydrous magnesium sulfate, concentrated, and recrystallized from methylene chloride. Consequently, compound 3 was obtained almost quantitatively (11.7 g).

(B) Synthesis of Compound 4: (R)-6,6'-Diiodo-2,2'-di(methoxymethyl)oxy-1,1'-binaphthyl Compound3 (8.75 g, 16.4 mmol) was dissolved in anhydrous tetrahydrofuran (80 ml). To this solution, approximately 1.5 M of n-butyllithium/hexane solution (32 ml, 49.2 mmol) was slowly added dropwise at −78° C. After the completion of the dropwise addition, the mixture was stirred for 30 minutes. To this solution was added dropwise a tetrahydrofuran (10 ml) solution of iodine (12.5g, 49.2 mmol). The reaction solution was stirred for approximately 12 hours while the temperature was gradually elevated to approximately room temperature.

Water was carefully added to terminate the reaction, after which the same volume of a 10% aqueous solution of sodium hydrogen sulfite was added while the solution was stirred for a while. When the color of the organic layer turned to a transparent yellow, the layer was separated, and washed with a saturated aqueous solution of sodium bicarbonate, water and a saturated aqueous solution of sodium chloride successively. The solution was thoroughly dried over anhydrous magnesium sulfate, concentrated, and then purified by silica gel column chromatography. Compound 4 was obtained (7.33 g, 71%).

(C) Synthesis of Compound 1: (R)-6,6'-(α,α,α)-Trifluoromethyl-2,2'-dihydroxy-1,1'-binaphthyl A large amount of trifluoromethyl copper reagent was prepared according to the method of D. J. Burton et al. (J. Am. Chem. Soc. 1985, 107, 5014–5015; J. Am. Chem. Soc. 1986, 108, 832–834), to which were added compound 4 (360 mg, 0.57 mmol), and stirred at 80° C. for 12 hours. To the reaction mixture were added benzene (50 ml) and water (50 ml), and stirred for one day for distribution. The organic layer was separated, washed with water and a saturated aqueous solution of sodium chloride, and then dried over anhydrous sodium sulfate. After concentration, the product was purified through column chromatography (benzene:hexane=1:1) and (R)-6,6'-(α,α,α)-trifluoromethyl-2,2'-di(methoxymethyl)oxy-1,1'-binaphthyl (296.5 mg, 98%) was obtained.

This substance was dissolved in methylene chloride (5 ml) and methanol (5 ml), and reacted by adding an anhydrous hydrochloric acid-methanol solution at 0° C., while the progress of there action was confirmed by TLC. When the starting material disappeared, the product was diluted with water and methylene chloride for distribution.

The organic layer was washed with a saturated aqueous solution of sodium bicarbonate, water and a saturated aqueous solution of sodium chloride, successively, dried over anhydrous sodium sulfate, and then purified by silica gel column chromatography. Compound 1 was obtained (quantitative).

The physical properties of compound 1 are as follows.

$^1$H-NMR (CDCl$_3$):δ=5.26 (s, 2H), 7.18 (d, 2H, J=8.5 Hz), 7.46 (d, 2H, J=8.5 Hz), 7.48 (d, 2H, J=8.8 Hz), 8.08 (d, 2H, J=8.8 Hz), 8.20 (s, 2H). $^{13}$C-NMR (CDCl$_3$): δ=110.7, 119.3, 123.3 (q, J=2.1 Hz), 124.3 (q, J=272.1 Hz), 125.0, 126.25 (q, J=4.1Hz), 126.29 (q, J=32.1 Hz), 128.3, 132.6, 134.9, 154.5. IR (KBr): 3465, 3038, 1633, 1311, 1198, 1152 cm$^{-1}$, Mp. 112–113° C.

Example 2

(R)-3,3'-(α,α,α)-Trifluoromethyl-2,2'-dihydroxy-1,1'-binaphthyl as compound 5 was synthesized according to the following reaction scheme.

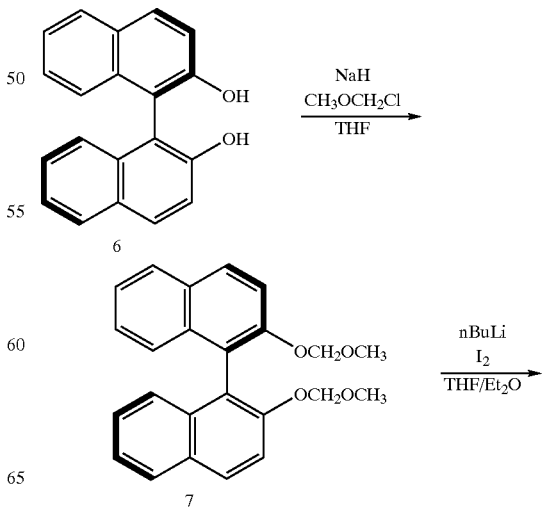

-continued

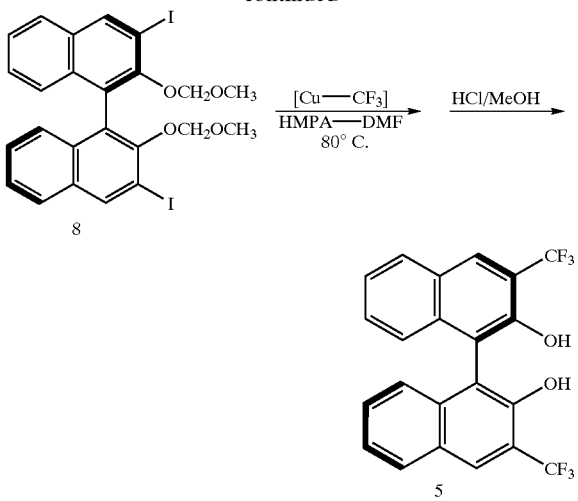

(A) Synthesis of Compound 7: (R)-2,2'-di(methoxymethyl)oxy-1,1'-binaphthyl

An oil suspension of sodium hydride (60%; 14g, 350 mmol) was washed with petroleum ether, and dried, after which anhydrous tetrahydrofuran (200 ml) was added. This solution was cooled to 0° C., and an anhydrous tetrahydrofuran solution (soluble amount) of (R)-2,2'-dihydroxy-1,1'-binaphthyl (compound 6; 10 g, 35 mmol) was added dropwise. After the completion of the dropwise addition, the mixture was stirred at the same temperature for 1 hour, and chloromethylether (26.6 ml, 350 mmol) was added. This mixture was stirred at room temperature until the starting material, compound 6, could no longer be identified by TLC.

After a small amount of methanol was added to terminate the reaction, ethyl acetate and a saturated aqueous solution of ammonium chloride were added for distribution. Subsequently, the organic layer was washed with water and a saturated aqueous solution of sodium chloride, successively. The organic layer was thoroughly dried over anhydrous magnesium sulfate, concentrated, and then recrystallized from methylene chloride. Consequently, compound 7 was obtained almost quantitatively (13 g).

(B) Synthesis of Compound 8: (R)-3,3'-Diiodo-2,2'-di(methoxymethyl)oxy-1,1'-binaphthyl Compound 7 (6.48 g, 17.3 mmol) was dissolved in anhydrous ether (200 ml); to the solution, approximately 1.5 M of a n-butyl lithium/hexane solution (33 ml, 49.5 mmol) was slowly added dropwise at 0° C. After the completion of the dropwise addition, the mixture was stirred at room temperature for 3 hours and cooled to 0° C. again, after which a tetrahydrofuran (10 ml) solution of iodine (12.3 g, 49.5 mmol) was added dropwise. The solution was stirred for approximately 12 hours while the temperature was gradually elevated to approximately room temperature. After water was carefully added to terminate the reaction, the same volume of a 10% aqueous solution of sodium hydrogen sulfite was added and stirred for a while. When the color of the organic layer turned to a transparent yellow, the layer was separated and washed with a saturated aqueous solution of sodium bicarbonate, water and a saturated aqueous solution of sodium chloride, successively. The product was thoroughly dried over anhydrous magnesium sulfate, concentrated, and then purified by silica gel column chromatography. Compound 8 was obtained (8.74 g, 80%).

(C) Synthesis of Compound 5: (R)-3,3'-(α,α,α)-trifluoromethyl-2,2'-dihydroxy-1,1'-binaphthyl A trifluoromethyl copper reagent was prepared in a large amount according to the method of D. J. Burton et al. (J. Am. Chem. Soc. 1985, 107, 5014–5015, J. Am. Chem. Soc. 1986, 108, 832–834), to which was added compound 8 (360 mg, 0.57 mmol); and stirred at 80° C. for 12 hours. To the reaction mixture were added benzene (50 ml) and water (50 ml), and stirred for one day for distribution. The organic layer was separated, washed with water and a saturated aqueous solution of sodium chloride, and dried over anhydrous sodium sulfate.

After concentration, the product was purified through column chromatography (benzene:hexane=1:1) to obtain (R)-6,6'-(α,α,α)-trifluoromethyl-2,2'-di(methoxymethyl)oxy-1,1'-binaphthyl. This compound was dissolved in methylene chloride (5 ml) and methanol (5 ml) and reacted by adding an anhydrous hydrochloric acid-methanol solution at 0° C., while the progress of the reaction was confirmed by TLC. When the starting material disappeared, the product was diluted with water and methylene chloride for distribution. The organic layer was washed with a saturated aqueous solution of sodium bicarbonate, water and a saturated aqueous solution of sodium chloride successively, dried over anhydrous sodium sulfate, and purified by silica gel column chromatography to obtain compound 5.

The physical properties of compound 5 are as follows.

$^1$H-NMR (CDCl$_3$):δ=5.34 (s, 2H), 7.12 (d, 2H, J=8.2 Hz), 7.44–7.51 (m, 4H), 8.00 (d, 2H, J=7.6 Hz), 8.20 (s, 2H). $^{13}$C-NMR (CDCl$_3$):δ=112.2, 118.8 (q, J=21.0 Hz), 123.3 (q, J=273.1 Hz), 123.9, 125.5, 127.8, 129.7, 130.0, 130.4 (q, J=5.2 Hz), 134.6, 149.4. IR (KBr): 3549, 3063, 1628, 1331, 1209, 1132 cm$^{-1}$, Mp. 241° C.

Example 3

Compound 1: (R)-6,6'-(α,α,α)-trifluoromethyl-2,2'-dihydroxy-1,1'-binaphthyl obtained in Example 1 was used as a component of an asymmetric metal catalyst with zirconium; a catalytic asymmetric Mannich-type reaction was conducted according to the following reaction formula to synthesize an aminocarbon derivative.

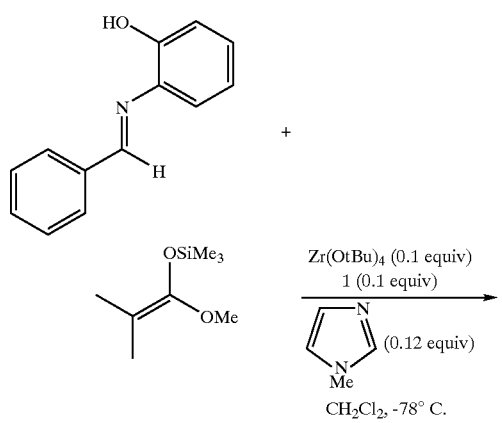

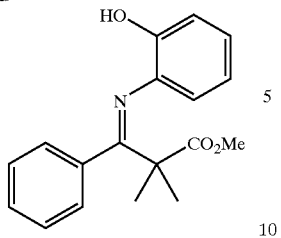

That is, a methylene chloride solution (0.25 ml) of zirconium tetra-t-butoxide (0.025 mmol) was first added to a methylene chloride solution (0.5 ml) of compound 1 (23.2 mg, 0.055 mmol) and 1-methylimidazole (2.5 mg, 0.030 mmol), and stirred at room temperature for 1 hour, to prepare a methylene chloride solution of an optically active zirconium catalyst.

This catalyst solution was cooled to −78° C., and a methylene chloride solution (1.0 ml) of N-benzylidene-2-hydroxyaniline (49.5 mg, 0.25 mmol) and 1-methoxy-1-trimethylsilyloxy-methyl-propene (52.3 mg, 0.30 mmol) was added. After 20 hours, the reaction was terminated with a saturated aqueous solution of sodium bicarbonate, and the organic layer was extracted with methylene chloride. This solution was concentrated, and stirred at 0° C. for 1 hour after adding dilute hydrochloric acid/tetrahydrofuran solution. The reaction was again terminated with a saturated aqueous solution of sodium bicarbonate, and treated according to conventional methods to obtain the product shown in the above-mentioned reaction formula (73.0 mg, yield 97%).

The optical purity of the resulting product was measured through high-performance liquid chromatography using an optically active column, and was found to be 91%, an excess ratio for the (R) compound.

INDUSTRIAL APPLICABILITY

As has been described in detail, provided by the invention of the present application are, a novel optically active binaphthol derivative useful as an asymmetric catalyst or the like, with which higher reaction yield and higher optical yield (selectivity) may be attained in asymmetric synthesis, an asymmetric catalyst using the same, and a method of asymmetric synthesis.

What is claimed is:

1. An optically active fluorinated binaphthol derivative represented by the following formula (I)

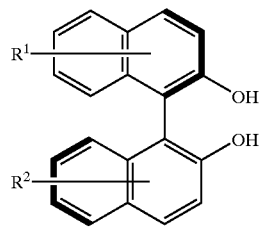

wherein $R^1$ and $R^2$ each represent a fluorinated hydrocarbon group.

2. The optically active fluorinated binaphthol derivative of claim 1, wherein the fluorinated hydrocarbon group of $R^1$ and $R^2$ is a perfluoroalkyl group.

3. A method for producing the optically active fluorinated binaphthol derivative of claim 2, comprising substituting the halogen atom (X) of an optically active halogenated binaphthol derivative represented by the following formula (II):

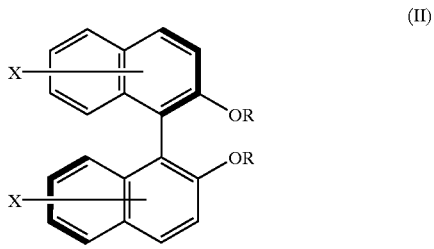

wherein X represents a halogen atom, and R represents a methoxymethyl group, with a perfluoroalkyl group, by reacting the compound represented by the above formula (11) with perfluoroalkyl copper reagent and eliminating the protective group (R) using anhydrous hydrochloric acid-methanol solution.

4. An asymmetric metal catalyst comprising the optically active fluorinated binaphthol derivative of claim 2 and zirconium.

5. A method of performing an asymmetric Mannich synthesis which comprises reacting an aldehyde compound with a silyl enol ether in the presence of the asymmetric metal catalyst of claim 4.

* * * * *